US007749490B2

(12) United States Patent
Sommer et al.

(10) Patent No.: US 7,749,490 B2
(45) Date of Patent: Jul. 6, 2010

(54) MUTANT IL-10

(75) Inventors: Jurg M. Sommer, Orinda, CA (US); Raymond A. Chavez, Alameda, CA (US); Kirk W. Johnson, Moraga, CA (US); Linda May Rothblum Watkins, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 11/920,711

(22) PCT Filed: May 26, 2006

(86) PCT No.: PCT/US2006/020863

§ 371 (c)(1),
(2), (4) Date: May 16, 2008

(87) PCT Pub. No.: WO2006/130580

PCT Pub. Date: Dec. 7, 2006

(65) Prior Publication Data

US 2009/0035256 A1 Feb. 5, 2009

Related U.S. Application Data

(60) Provisional application No. 60/686,272, filed on May 31, 2005.

(51) Int. Cl.
*C07K 14/00* (2006.01)
*A61K 45/00* (2006.01)

(52) U.S. Cl. ...................................... 424/85.2; 530/351

(58) Field of Classification Search ....................... None

See application file for complete search history.

(56) References Cited

U.S. PATENT DOCUMENTS 6,428,985 B1 8/2002 Bromberg et al.

OTHER PUBLICATIONS

Goodman, et al., "Synthesis and Characterization of Rat Interleukin-10 (IL-10) CDNA Clones From the RNA of Cultured OX8-negative OX22-negative Thoracic Duct T Cells", Biochemical and Biophysical Research Communications, 189(1):1-7 (1992).

Vieira, et al. "Isolation and Expression of Human Cytokine Synthesis Inhibitory Factor CDNA Clones: Homology to Epstein-Barr Virus Open Reading Frame BCRF1", Proceedings of the National Academy of Sciences of USA, National Academy of Science, Washington, DC, US, 88:1172-1176 (1991).

*Primary Examiner*—Dong Jiang
(74) *Attorney, Agent, or Firm*—Robins & Pasternak LLP

(57) ABSTRACT

IL-10 sequence variants are disclosed that retain the therapeutically desirable anti-inflammatory properties of wild-type IL-10 but do not retain the hemoatopoeitic cell regulatory and cell proliferative activities. The mutant IL-10 polypeptides of the invention are used in methods of treating diseases involving inflammatory response, including neuropathic pain and other neurological disorders.

4 Claims, 4 Drawing Sheets

```
                                     1                                                  50
  Wild type human IL-10     (1)  MHSSALLCCLVLLTGVRASPGQGTQSENSCTHFPGNLPNMLRDLRDAFSR
    Wild type rat IL-10     (1)  MLGSALLCCLLLLAGVKTSKGHSIRGDNNCTHFPVSQTHMLRELRAAFSQ
Mutant rat IL-10 (F129S)    (1)  MLGSALLCCLLLLAGVKTSKGHSIRGDNNCTHFPVSQTHMLRELRAAFSQ

                                 51                                                 100
  Wild type human IL-10    (51)  VKTFFQMKDQLDNLLLKESLLEDFKGYLGCQALSEMIQFYLEEVMPQAEN
    Wild type rat IL-10    (51)  VKTFFQKKDQLDNIVLTDSLLQDFKGYLGCQALSEMIKFYLVEVMPQAEN
Mutant rat IL-10 (F129S)   (51)  VKTFFQKKDQLDNILLTDSLLQDFKGYLGCQALSEMIKFYLVEVMPQAEN

                                 101                         129                    150
  Wild type human IL-10   (101)  QDPDIKAHVNSLGENLKTLRLRLRRCHRFLPCENKSKAVEQVKNAFNKLQ
    Wild type rat IL-10   (101)  HGPEIKEHLNSLGEKLKTLWIQLRRCHRFLPCENKSKAVEQVKNDFNKLQ
Mutant rat IL-10 (F129S)(101)  HGPEIKEHLNSLGEKLKTLWIQLRRCHRSLPCENKSKAVEQVKNDFNKLQ

                                 151                       178
  Wild type human IL-10   (151)  EKGIYKAMSEFDIFINYIEAYMTMKIRN (SEQ ID NO:3)
    Wild type rat IL-10   (151)  DKGVYKAMNEFDIFINCIEAYVTLKMKN (SEQ ID NO:2)
Mutant rat IL-10 (F129S)(151)  DKGVYKAMNEFDIFINCIEAYVTLKMKN (SEQ ID NO:1)
```

Fig. 1

```
                              SEQUENCE LISTING


<160> NUMBER OF SEQ ID NOS: 3

<210> SEQ ID NO 1
<211> LENGTH: 178
<212> TYPE: PRT
<213> ORGANISM: artificial
<220> FEATURE:
<223> OTHER INFORMATION: rat IL-10 F129S

<400> SEQUENCE: 1

Met Leu Gly Ser Ala Leu Leu Cys Cys Leu Leu Leu Leu Ala Gly Val
1               5                   10                  15

Lys Thr Ser Lys Gly His Ser Ile Arg Gly Asp Asn Asn Cys Thr His
            20                  25                  30

Phe Pro Val Ser Gln Thr His Met Leu Arg Glu Leu Arg Ala Ala Phe
        35                  40                  45

Ser Gln Val Lys Thr Phe Phe Gln Lys Lys Asp Gln Leu Asp Asn Ile
    50                  55                  60

Leu Leu Thr Asp Ser Leu Leu Gln Asp Phe Lys Gly Tyr Leu Gly Cys
65                  70                  75                  80
```

-continued

```
Gln Ala Leu Ser Glu Met Ile Lys Phe Tyr Leu Val Glu Val Met Pro
                85                  90                  95

Gln Ala Glu Asn His Gly Pro Glu Ile Lys Glu His Leu Asn Ser Leu
            100                 105                 110

Gly Glu Lys Leu Lys Thr Leu Trp Ile Gln Leu Arg Arg Cys His Arg
        115                 120                 125

Ser Leu Pro Cys Glu Asn Lys Ser Lys Ala Val Glu Gln Val Lys Asn
    130                 135                 140

Asp Phe Asn Lys Leu Gln Asp Lys Gly Val Tyr Lys Ala Met Asn Glu
145                 150                 155                 160

Phe Asp Ile Phe Ile Asn Cys Ile Glu Ala Tyr Val Thr Leu Lys Met
                165                 170                 175

Lys Asn


<210> SEQ ID NO 2
<211> LENGTH: 178
<212> TYPE: PRT
<213> ORGANISM: Rattus norvegicus

<400> SEQUENCE: 2

Met Leu Gly Ser Ala Leu Leu Cys Cys Leu Leu Leu Leu Ala Gly Val
1               5                   10                  15

Lys Thr Ser Lys Gly His Ser Ile Arg Gly Asp Asn Asn Cys Thr His
            20                  25                  30

Phe Pro Val Ser Gln Thr His Met Leu Arg Glu Leu Arg Ala Ala Phe
        35                  40                  45

Ser Gln Val Lys Thr Phe Phe Gln Lys Lys Asp Gln Leu Asp Asn Ile
    50                  55                  60

Val Leu Thr Asp Ser Leu Leu Gln Asp Phe Lys Gly Tyr Leu Gly Cys
65                  70                  75                  80

Gln Ala Leu Ser Glu Met Ile Lys Phe Tyr Leu Val Glu Val Met Pro
                85                  90                  95

Gln Ala Glu Asn His Gly Pro Glu Ile Lys Glu His Leu Asn Ser Leu
            100                 105                 110

Gly Glu Lys Leu Lys Thr Leu Trp Ile Gln Leu Arg Arg Cys His Arg
        115                 120                 125

Phe Leu Pro Cys Glu Asn Lys Ser Lys Ala Val Glu Gln Val Lys Asn
    130                 135                 140

Asp Phe Asn Lys Leu Gln Asp Lys Gly Val Tyr Lys Ala Met Asn Glu
145                 150                 155                 160

Phe Asp Ile Phe Ile Asn Cys Ile Glu Ala Tyr Val Thr Leu Lys Met
                165                 170                 175

Lys Asn


<210> SEQ ID NO 3
<211> LENGTH: 178
<212> TYPE: PRT
<213> ORGANISM: Homo sapiens

<400> SEQUENCE: 3

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
```

-continued

```
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

MUTANT IL-10

CROSS-REFERENCE TO RELATED APPLICATION

This application is a 35 U.S.C. §371 filing of PCT/US2006/020863, filed May 26, 2006, from which priority is claimed under 35 U.S.C. §120, which in turn claims the benefit under 35 USC §119(e)(1) of provisional application 60/686,272, filed May 31, 2005, which applications are hereby incorporated by reference in their entireties.

STATEMENT REGARDING FEDERALLY SPONSORED RESEARCH OR DEVELOPMENT

This invention was made with government support under DA015656, DA018156, and DA015642, awarded by the National Institutes of Health. The government has certain rights in the invention.

TECHNICAL FIELD

This invention relates to a mutant form of interleukin 10 (IL-10) lacking some of the functions of wild-type IL-10, and compositions and methods for use thereof.

BACKGROUND

Interleukin-10 (IL-10), also known as cytokine synthesis inhibitory factor (CSIF), is normally expressed in T cells, macrophages, monocytes, dendritic cells, mast cells, B cells, eosinophils, keratinocytes, epithelial cells, and various tumor cell lines (reviewed by Williams et al. (2004) *Immunology* 113:281-92). IL-10 has anti-inflammatory properties that may be exploited for the treatment of a number of illnesses. IL-10 is naturally synthesized in the CNS and acts to limit clinical symptoms of stroke, multiple sclerosis, Alzheimer's, and meningitis. In particular, IL-10 induces anergy in brain-infiltrating T cells by inhibiting cell signaling through CD28-CD80/86 costimulation and promotes survival of neurons and glial cells by blocking proapoptotic cytokines. Strle et al. (2001) *Crit. Rev. Immunol.* 21:427-49. Further discussion of the use of IL-10 for the treatment of neuropathic pain can be found in Milligan et al. (2005) *Molecular Pain* 1:9. IL-10 has also been proposed as therapy for a number of other diseases for which anti-inflammatory activity is predicted to be beneficial.

Despite these advantageous anti-inflammatory properties, IL-10 elicits side effects that have limited its clinical development. For example, the cell proliferative activity of IL-10 is often undesirable, particularly when considering systemic administration.

Thus, there remains a need for new therapeutic approaches for treating neuropathic pain, neurological disorders and other inflammatory disorders that do not have the adverse side effects associated with administration of wild-type IL-10.

SUMMARY OF ME INVENTION

The present invention provides proteins, compositions and methods for treating neuropathic pain, neurological disorders and other inflammatory disorders using a mutant form of IL-10 wherein the residue present at a position corresponding to amino acid position 129 of SEQ ID NOS:2 and 3 is replaced with another amino acid. In preferred embodiments, the amino acid phenylalanine normally present at amino acid position 129 of rat and human IL-10 is replaced with the amino acid serine. This mutation is termed "F129S." Thus, this mutant IL-10 polypeptide is referred to herein as "rIL-10 (F129S)." The corresponding mutant human IL-10 polypeptide is referred to herein as "hIL-10 (F129S)."

In other embodiments, the same mutation is introduced (or selected for) at the analogous position in an IL-10 protein derived from another species to give a mutant IL-10 that can be tested to determine whether it exhibits reduced undesirable activities.

Thus, in certain embodiments, the invention is directed to a mutant IL-10 polypeptide comprising a substitution of the amino acid occurring at a position corresponding to position 129 of SEQ ID NO:2 or SEQ ID NO:3. In certain embodiments, the polypeptide comprises a substitution of serine for the amino acid occurring at the position corresponding to position 129 of SEQ ID NO:2 or SEQ ID NO:3. In additional embodiments, the polypeptide comprises a substitution of serine for phenylalanine at position 129 of SEQ ID NO:2 or SEQ ID NO:3.

In yet further embodiments, the IL-10 polypeptide comprises the amino acid sequence of SEQ ID NO:1. In certain embodiments, the polypeptide consists of the amino acid sequence of SEQ ID NO:1.

Other mutations at the same position 129 may also exhibit desirable properties. Mutant IL-10 proteins with substitution of the wild-type phenylalanine with threonine, alanine or cysteine, for example, may exhibit properties similar to those exhibited by rIL-10 (F129S).

In certain embodiments, a therapeutic amount of the mutant IL-10 of the invention is administered to a subject to treat neuropathic pain, or other neurological disorder selected from the group consisting of Alzheimer's disease, amyotrophic lateral sclerosis (Lou Gehrig's disease), Parkinson's disease, multiple sclerosis and Huntington's disease. Treatment of subjects having more than one pathological condition is also envisioned.

In other embodiments, a therapeutic amount of the mutant IL-10 of the invention is administered to a subject to treat an inflammatory disease or condition, such as rheumatoid arthritis. The methods and compositions of the present invention can be used to treat or prevent septic shock, inflammatory bowel disease, Crohn's disease, rheumatoid arthritis, uveitis, psoriasis, ulcerative colitis, or other inflammatory condition.

In various embodiments, the mutant IL-10 of the invention is delivered as a purified protein, or as a nucleic acid vector comprising a sequence encoding the mutant IL-10. The nucleic acid vector can be a plasmid or a viral particle carrying a viral vector.

In one embodiment, the nucleic acid vector is an adeno-associated virus(AAV) vector having one or more AAV inverted terminal repeat (ITR) sequence elements and control elements for directing expression of the sequence encoding the mutant IL-10 in a target cell, which AAV vector can be administered either as a plasmid ("naked" DNA) or as packaged in an AAV particle.

In another embodiment, the invention relates to a method of treating a subject undergoing immunostimulatory anti-cancer therapy, for example treatment with interleukin-2 (IL-2), comprising administering to said subject a mutant IL-10 having an F129A mutation, whereby the mutant IL-10 acts to suppress the release of certain cytokines that would otherwise be released in response to the immunostimulatory anti-cancer therapy.

In a further embodiment, the invention relates to use of a mutant IL-10 polypeptide of the invention in a high throughput screening assay to discover anti-inflammatory agents with desirable properties.

These and other embodiments of the subject invention will readily occur to those of skill in the art in view of the disclosure herein.

BRIEF DESCRIPTION OF THE FIGURES

FIG. 1 presents an alignment of human (Vieira et al. (1991) *Proc Natl Acad Sci USA.* 88:1172-6), rat (Goodman et al. (1992) *Biochem Biophys Res Commun.* 189:1-7) and mutant rat (F129S) interleukin-10 precursor sequences. The phenylalanine to serine substitution in the mutated rat sequence is indicated in bold at position 129. The mature IL-10 protein extends from residue 19 (serine) to 178 (asparagine).

DETAILED DESCRIPTION OF THE INVENTION

Figure 2:
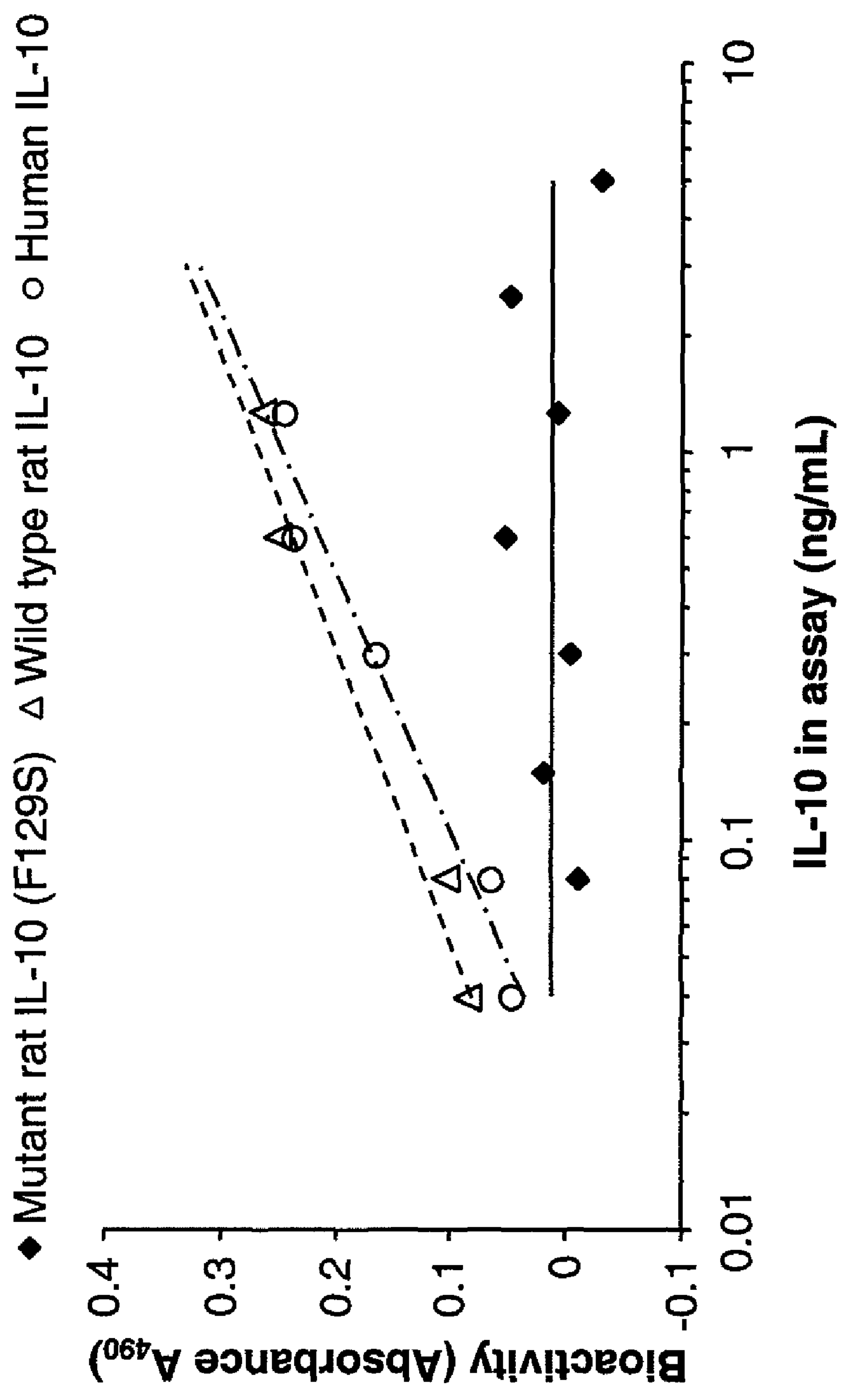
FIG. 2 presents data demonstrating the lack of bioactivity of the rIL-10 (F129S) in an MC/9 cell proliferation assay. Details are provided at Example 1.

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein are hereby incorporated by reference in their entireties.

The following amino acid abbreviations are used throughout the text:

Alanine: Ala (A) Arginine: Arg (R)
Asparagine: Asn (N) Aspartic acid: Asp (D)
Cysteine: Cys (C) Glutamine: Gln (Q)
Glutamic acid: Glu (E) Glycine: Gly (G)
Histidine: His (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)

I. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise.

The term "derived from" is used herein to identify the original source of a molecule but is not meant to limit the method by which the molecule is made which can be, for example, by chemical synthesis or recombinant means.

The terms "variant," "analog" and "mutein" refer to biologically active derivatives of the reference molecule, that retain desired activity, such as anti-inflammatory activity as described herein. In general, the terms "variant" and "analog" in reference to a polypeptide refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., *Chem Biol.* (2000) 7:463-473; and Simon et al., *Proc. Natl. Acad. Sci. USA* (1992) 89:9367-9371 for descriptions of peptoids). Preferably, the analog or mutein has at least the same anti-inflammatory activity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "derivative" is intended any suitable modification of the reference molecule of interest or of an analog thereof, such as sulfation, acetylation, glycosylation, phosphorylation, polymer conjugation (such as with polyethylene glycol), or other addition of foreign moieties, so long as the desired biological activity (e.g., clotting activity, inhibition of TFPI activity) of the reference molecule is retained.

By "fragment" is intended a molecule consisting of only a part of the intact full-length sequence and structure. A fragment of a polypeptide can include a C-terminal deletion an N-terminal deletion, and/or an internal deletion of the native polypeptide. Active fragments of a particular protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the full-length sequence, provided that the fragment in question retains biological activity, such as anti-inflammatory activity.

"Substantially purified" generally refers to isolation of a substance such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National Biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

By "vector" is meant any genetic element, such as a plasmid, phage, transposon, cosmid, chromosome, virus, virion, etc., which is capable of replication when associated with the proper control elements and which can transfer gene sequences to cells. Thus, the term includes cloning and expression vehicles, as well as viral vectors.

By "recombinant vector" is meant a vector that includes a heterologous nucleic acid sequence which is capable of expression in vivo.

By "recombinant virus" is meant a virus that has been genetically altered, e.g., by the addition or insertion of a heterologous nucleic acid construct into the particle.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52 :456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species.

The term "patient," refers to a living organism suffering from or prone to a condition that can be prevented or treated by administration of the mutant IL-10 of the invention, and includes both humans and animals. The terms "subject", "individual" or "patient" are used interchangeably herein and refer to a vertebrate, preferably a mammal. Mammals include, but are not limited to, murines, rodents, simians, humans, farm animals, sport animals and certain pets.

Unless stated otherwise, the terms "protein" "polypeptide" and "peptide" are used interchangeably herein to refer to a polymer of two or more amino acids joined by peptide bonds. Similarly, as used herein, "an IL-10" refers to such a protein. When referring to IL-10 proteins derived from rat or human IL-10 the prefixes "r" and "h" are used (rIL-10, hIL-10). When no such species-specific prefix is used IL-10 refers generically to IL-10 of any type or origin. The terms "wild-type," "wt" and "native" are used interchangeably herein to refer to the sequence of the protein (e.g. IL-10) as commonly found in nature in the species of origin of the specific IL-10 in question. Protein sequence variants are presented in the typical nomenclature with the original amino acid, followed by the position number and the new amino acid (e.g. "F129S").

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

By "therapeutically effective dose or amount" of the mutant IL-10 of the invention is intended an amount that, when administered as described herein, brings about a positive therapeutic response, such as reduced pain. In the context of the treatment of certain disorders, such as neurodegenerative disease, a slowing or stopping of the progression of a symptom can comprise a positive therapeutic response when the symptom would otherwise be expected to progress in the absence of treatment. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

"Treatment" or "treating" pain includes: (1) preventing pain, i.e. causing pain not to develop or to occur with less intensity in a subject that may be exposed to or predisposed to pain but does not yet experience or display pain, (2) inhibiting pain, i.e., arresting the development or reversing pain, or (3) relieving pain, i.e., decreasing the amount of pain experienced by the subject.

By "treating existing pain" is meant relieving or reversing pain in a subject that has been experiencing pain for at least 24 hours, such as for 24-96 hours or more, such as 25 . . . 30 . . . 35 . . . 40 . . . 45 . . . 48 . . . 50 . . . 55 . . . 65 . . . 72 . . . 80 . . . 90 . . . 96 . . . 100, etc. hours. The term also intends treating pain that has been occurring long-term, such as for weeks, months or even years

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

A. General Overview

IL-10 is an immunosuppressive cytokine that suppresses release and function of proinflammatory cytokines such as IL-1, IL-2, IL-6, tumor necrosis factor α (TNFα), and GM-CSF. Williams et al. (2004) *Immunology* 113:281-92. In this manner Il-10 acts as a normal endogenous feedback system to control immune responses and inflammation. IL-10 also acts as a chemotactic factor towards CD8+T cells, and is able to inhibit antigen-specific T cell proliferation. Some of the activities of IL-10 require different portions of the protein sequence (e.g. C-terminus vs. N-terminus, Gesser et al. (1997) *Proc Natl Acad Sci USA*. 94:14620-5) and it is thus assumed that mutant forms of IL-10 could be devised which perform only a selected subset of the IL-10 functions.

Eight other cellular cytokines have been identified that are structurally related to IL-10, but none appear to have anti-inflammatory function. Zdanov (2004) *Curr Pharm Des*. 10:3873-84. Viral homologs that are related to IL-10 and act to modulate the host immune response have been identified. Yoon et al. (2005) *Structure* 13:551-64. These viral homologs encode some IL-10-like anti-inflammatory activities, but they do not mimic all of IL-10's functions. As such, the viral homologs may have interesting therapeutic properties, but their sequences have significantly diverged from the mammalian IL-10 homologs and would likely be immunogenic. A comparison of viral and human IL-10 sequences shows identities ranging from 27% for the cytomegalovirus-encoded IL-10 to 83% for the Epstein-Barr virus-encoded IL-10. The present invention demonstrates that a single amino acid substitution is sufficient to alter the activity profile of IL-10 to make it a highly specific therapeutic anti-inflammatory protein, likely with reduced side effects and reduced immunogenic potential.

The present invention relates to a mutant IL-10 that has reduced cell proliferation activity, but that retains certain anti-inflammatory activities that are useful in treatment of neuropathic pain, neurological disorders and other inflammatory disorders. In one embodiment, a single amino acid change in the rat IL-10 peptide sequence (F129S) surprisingly limits the spectrum of activities to a subset of classic IL-10 cytokine activities. Such mutated forms of IL-10 are expected to retain desirable therapeutic activities without dose-limiting side effects. Other mutations in IL-10 (at the isoleucine normally present at position 87) have been reported to have a similar effect on the IL-10 activity profile. U.S. Pat. No. 6,428,985.

In various aspects, the present invention relates to mutant IL-10 proteins that perform a subset of the IL-10 functions found in the native protein; shorter IL-10 peptide sequences derived from mutant IL-10 proteins, which peptides mimic a subset of native IL-10 functions; and DNA or RNA expression vectors that encode and direct the expression of the mutant IL-10 protein sequences of the invention.

Figure 3:
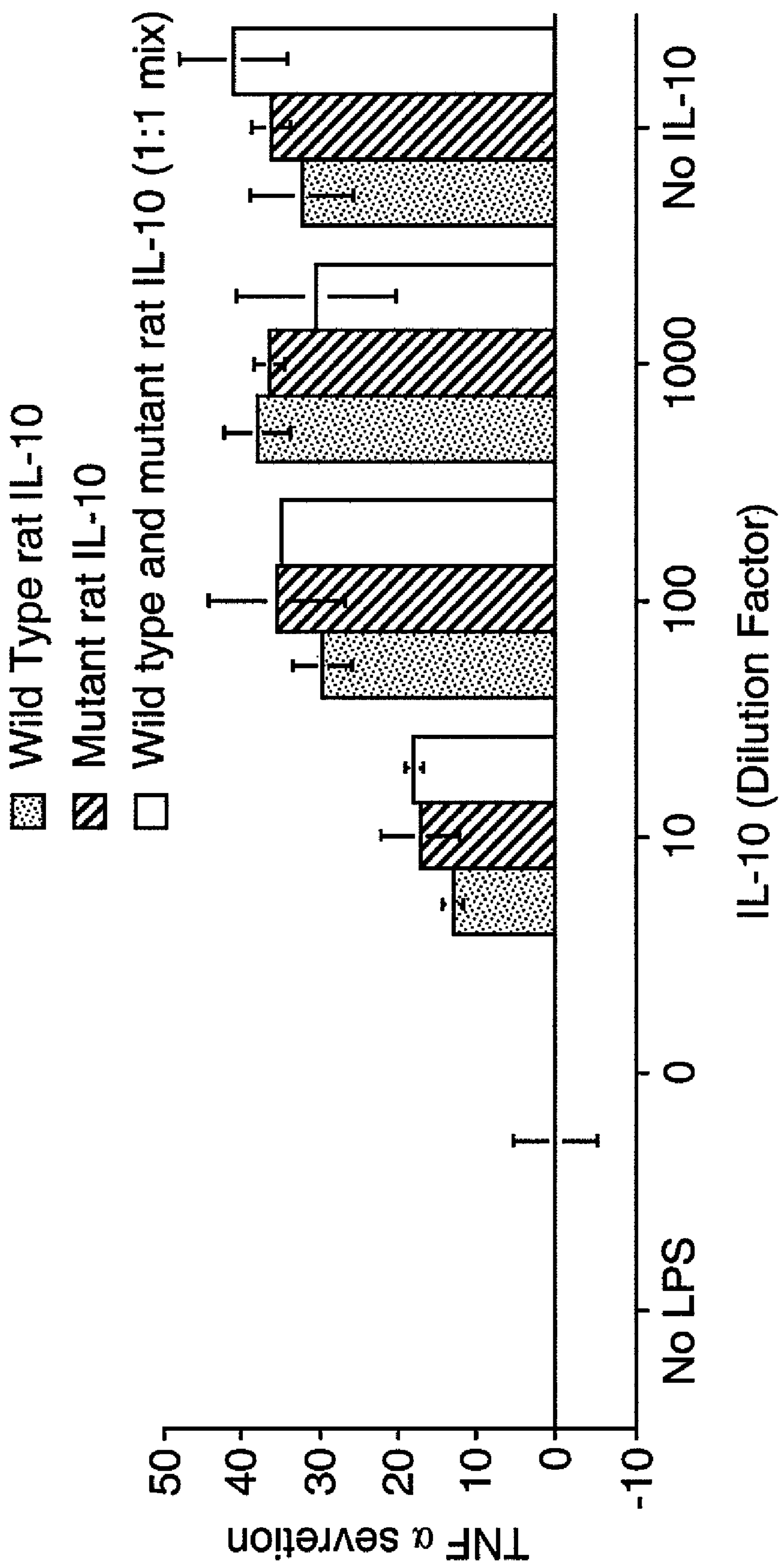
FIG. 3 presents data demonstrating that rIL-10 (F129S) suppresses TNFα secretion in a transformed glial cell line in vitro. Details are provided at Example 2.
Figure 4:
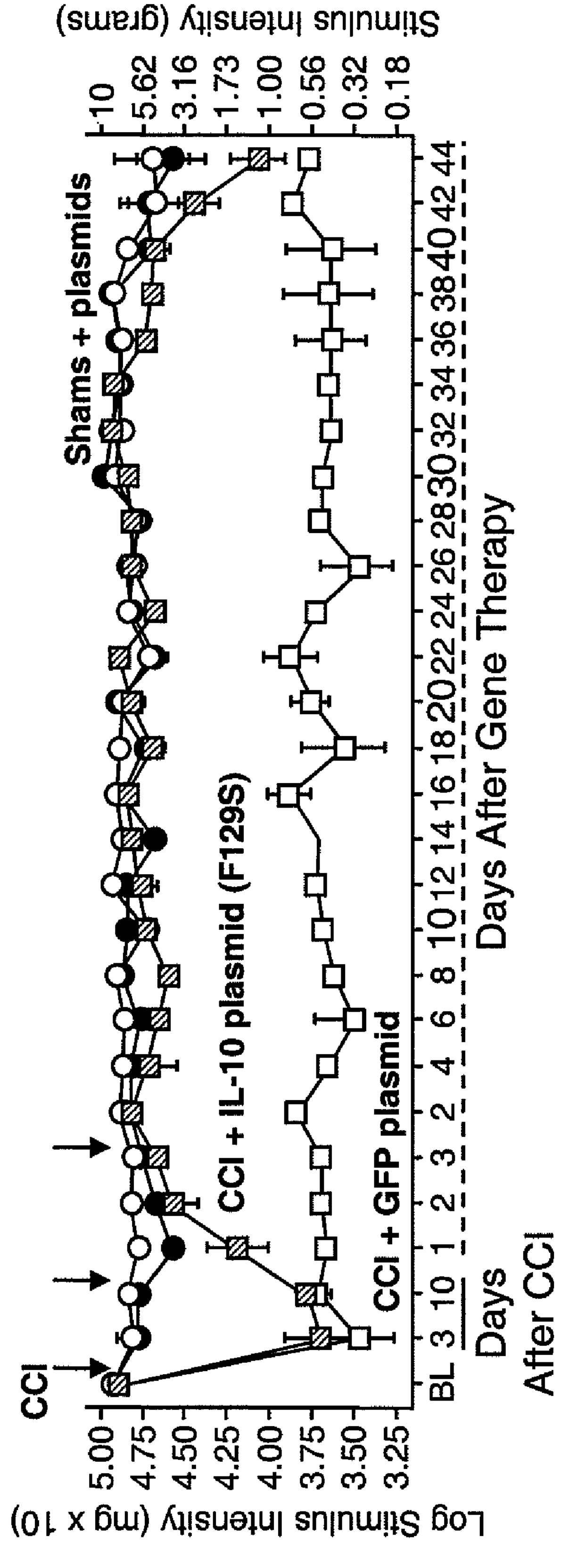
FIG. 4 presents data demonstrating that mutant rIL-10 (F129S) is capable of reversing mechanical allodynia in a common animal model for neuropathic pain (CCI—discussed in greater detail at Example 3). Symbols are as follow: open circles (○)=no CCI-+GFP plasmid; filled circles (●)=no CCI+rIL-10 (F129S) plasmid; open squares (□)=CCI+GFP plasmid; filled squares (■)=CCI+rIL-10 (F129S) plasmid. Details are provided at Example 3.

In one embodiment of the present invention, a phenylalanine at position 129 of the rat IL-10 precursor protein is replaced with a serine ("F129S"). FIG. 1. This mutant IL-10 has reduced activity in an in vitro cell proliferation assay (MC/9 assay, FIG. 2) but retains the ability to suppress TNFα secretion in an immortalized rat microglial cell (FIG. 3). Results of pharmacological evaluations indicate retention of cytokine synthesis inhibitory activity with reduced hematopoietic cell regulatory properties. In vivo analysis in rat models of neuropathic pain caused by nerve injuries or nerve constriction shows reduction in pain allodynia with long-term efficacy when the mutant IL-10 is expressed from a plasmid injected intrathecally (FIG. 4).

The F129S substitution is in a highly conserved region of the IL-10 protein (FIG. 1) and the homologous mutation in the human IL-10 protein would therefore be expected to function similarly in the human host. Analogous mutations in IL-10 homologs from other species may also be modified to incorporate an F to S substitution at the position corresponding to position 129 in the human and rat sequences, and then tested for a favorable activity profile.

In one embodiment the IL-10 (F129S) is produced as a protein and administered directly as an anti-inflammatory agent. In another embodiment IL-10 (F129S) is delivered by gene therapy using a vector encoding IL-10 (F129S), which vector can be a plasmid or a virus particle.

In another embodiment, the mutant IL-10 of the present invention is used in combination with an anti-cancer drug, such as IL-2. The rationale for this approach is based on the observation that native IL-10 disables antigen-presenting (AP) and T-cell activation by inhibiting expression of MHC class II, CD80, CD86 on macrophages and dendritic cells, and by inhibiting CD4+ T cells by suppressing IL-2, INF-γ, IL-4, IL-5 production. Williams et al. (2004) *Immunology* 113:281-92. The IL-10 mutants of the present invention, which do not possess these activities but retain cytokine suppressive activities, are used in cancer treatment in combination with immunostimulatory agents such as IL-2 to effect induction of natural killer (NK) cells while limiting cytokine release syndrome, a common side effect in IL-2 cancer treatment. This embodiment illustrates that the mutant IL-10 proteins of the present invention have the advantage when used as anti-inflammatory agents, particularly for embodiments involving systemic delivery, that they may be administered with less chance of adverse side effects. Because rIL-10 (F129A) exhibit reduction in some of the activities believed to lead to adverse side effects, it is more likely that this mutant IL-10 can be used in subjects at therapeutic doses without triggering such side effects.

In another aspect, the invention relates to use of the mutant IL-10 proteins of the invention as reagents in high throughput screening of drug candidates, for example an assay to find IL-10 receptor agonists that specifically reduce proinflammatory cytokine expression with minimal side effects. In vitro assays can be established as a readout for many of IL-10's biological functions. Gesser et al. (1997) *Proc Natl Acad Sci USA.* 94:14620-5. In principle, such assays can be used for screening molecular entities that may act as IL-10 receptor agonists mimicking IL-10 anti-inflammatory activities. Binding assays typically allow more efficient initial screening for drug leads than bioassays. To distinguish a potential lead compound with anti-inflammatory properties from those that also mimic undesirable IL-10 activities, a mutant form of the IL-10 protein with the desired properties would be used. Thus in one embodiment of the present invention, in vitro binding assays using the native form of the IL-10 protein and a version of the IL-10 carrying the F129S mutation are used to screen for drug leads that compete for binding of IL-10 to target cells with the same selectivity as IL-10 (F129S).

B. Mutant IL-10

In one embodiment, the mutant IL-10 of the present invention is a variant of wild-type rat IL-10 (rIL-10) having an F129S substitution (rIL-10 (F219S)). The sequence of rIL-10 (F129S) is:

```
                                                          (SEQ ID NO:1)
(1)    MLGSALLCCLLLLAGVKTSKGHSIRGDNNCTHFPVSQTHMLRELRAAFSQ

(51)   VKTFFQKKDQLDNILLTDSLLQDFKGYLGCQALSEMIKFYLVEVMPQAEN

(101)  HGPEIKEHLNSLGEKLKTLWIQLRRCHRSLPCENKSKAVEQVKNDFNKLQ

(151)  DKGVYKAMNEFDIFINCIEAYVTLKMKN                       (178)
```

The mutation relative to wild-type rIL-10 is shown as the bold-underlined serine residue at position 129. Position 129 in wild-type rIL-10 is phenylalanine. The sequences of wild-type and mutant rat IL-10, as well as the wild-type human IL-10, are also provided at FIG. 1 where they are optimally aligned.

The mutant IL-10 of the present invention can be delivered by any method know in the art, including direct administration of the mutant IL-10 protein and gene therapy with a vector encoding the mutant IL-10 protein. Gene therapy may be accomplished using plasmid DNA or a viral vector, such as an adeno-associated virus vector, an adenovirus vector, a retroviral vector, etc. In some embodiments, the viral vectors of the invention are administered as virus particles, and in others they are administered as plasmids (e.g. as "naked" DNA).

Mutant IL-10 proteins of the present invention include rat and human IL-10 variants, for which the corresponding wild-type sequences are disclosed at NCBI accession numbers NM012854, L02926, X60675 (rat) and NM000572, U63015, AF418271, AF247603, AF247604, AF247606, AF247605, AY029171, UL16720 (human).

Additional mutant IL-10 proteins of the present invention can be derived from other known IL-10 proteins by introducing the F129S mutation of the rat and human IL-10 embodiments the corresponding amino acid in the other IL-10 sequence. One of skill in the art would recognize that although the numbering of the analogous amino acids may vary from one IL-10 variant to another (e.g. from species to species), the position corresponding to F129 can be determined by calculating the optimal alignment of the IL-10 sequence in question with the rat and human sequences. Methods of performing such alignments of protein sequences are well known in the art. The F129S mutation may then be introduced into the candidate IL-10 sequence at the nucleic acid (DNA) level using site-directed mutagenesis methods employing synthetic oligonucleotides, which methods are also well known in the art.

Determination of the DNA mutations necessary to effect the desired amino acid change is within the skill in the art, and involves replacement of a codon for phenylalanine (e.g. TTC, TTT) with a codon for serine (e.g. TCA, TCC, TCG, TCT, ACG, ACT) at the desired position. In one embodiment, the serine codon is created by a single "T to C" base change (TCC or TCT). In another embodiment, the serine codon selected is the most commonly used serine codon in the organism in which the mutant IL-10 protein is to be expressed (e.g. the subject or the organism used for protein production). The resulting DNA constructs carrying the desired mutation can then be used directly in gene therapy or can be used to produce recombinant IL-10 protein.

Although not all such newly created mutant IL-10 proteins will necessarily have the desired mixture of wild-type IL-10 functions, it is within the skill in the art, in light of the present disclosure, to perform tests on such mutants to determine whether they retain anti-inflammatory function (e.g. using the TNFα secretion assay disclosed at Example 2) while having reduced cell proliferative activity (e.g. using the MC/9 cell proliferation assay disclosed at Example 1).

Exemplary IL-10 sequences that may be of use in constructing a mutant IL-10 of the present invention include IL-10 homologues isolated from the herpesviruses such as from Epstein-Barr virus (see, e.g., Moore et al., *Science* (1990) 248:1230-1234; Hsu et al., *Science* (1990) 250:830-832; Suzuki et al., *J. Exp. Med.* (1995) 182:477-486), Cytomegalovirus (see, e.g., Lockridge et al., *Virol.* (2000) 268:272-280; Kotenko et al., *Proc. Natl. Acad. Sci. USA* (2000) 97:1695-1700), and equine herpesvirus (see, e.g., Rode et al., *Virus Genes* (1993) 7:111-116), as well as the IL-10 homologue from the OrF virus (see, e.g., Imlach et al., *J. Gen. Virol.* (2002) 83:1049-1058 and Fleming et al., *Virus Genes* (2000) 21:85-95). Other representative IL-10 sequences include the sequences described in NCBI accession numbers NM010548, AF307012, M37897, M84340 (mouse sequences); U38200 (equine); U39569, AF060520 (feline sequences); U00799 (bovine); U11421, Z29362 (ovine sequences); L26031, L26029 (macaque sequences); AF294758 (monkey); U33843 (canine); AF088887, AF068058 (rabbit sequences); AF012909, AF120030 (woodchuck sequences); AF026277 (possum); AF097510 (guinea pig); U11767 (deer); L37781 (gerbil); AB107649 (llama and camel).

Polynucleotides encoding the desired IL-10 sequence can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. The gene of interest can also be produced synthetically, rather than cloned, based on the known sequences. The molecules can be designed with appropriate codons for the particular sequence. The complete sequence is then assembled from overlapping oligonucleotides prepared by standard methods and assembled into a complete coding sequence. See, e.g., Edge, *Nature* (1981) 292:756; Nambair et al., *Science* (1984) 223:1299; and Jay et al., *J. Biol. Chem.* (1984) 259:6311.

Desired nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. One method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., *Proc. Natl. Acad. Sci. USA* (1991) 88:4084-4088. Additionally, oligonucleotide-directed synthesis (Jones et al., *Nature* (1986) 54:75-82), oligonucleotide directed mutagenesis of preexisting nucleotide regions (Riechmann et al., *Nature* (1988) 332:323-327 and Verhoeyen et al., *Science* (1988) 239:1534-1536), and enzymatic filling-in of gapped oligonucleotides using $T_4$ DNA polymerase (Queen et al., *Proc. Natl. Acad. Sci. USA* (1989) 86:10029-10033) can be used to provide molecules for use in the subject methods.

C. Therapeutic Indications

The anti-inflammatory properties of IL-10 make it a candidate for therapy for neuropathic pain and neurodegenerative disorders such as Parkinson's disease, amyelotrophic lateral sclerosis (ALS) and multiple sclerosis (MS), each of which involves an inflammatory response that IL-10 may attenuate. Other neurological disorders that may be treatable by IL-10 include, but are not limited to, fatal familial insomnia, Rasmussen's encephalitis, Down's syndrome, Huntington's disease, Gerstmann-Straussler-Scheinker disease, tuberous sclerosis, neuronal ceroid lipofuscinosis, subacute sclerosing panencephalitis, Lyme disease; tse tse's disease (African Sleeping Sickness), HIV dementia, bovine spongiform encephalopathy ("mad cow" disease); Creutzfeldt Jacob disease; Herpes simplex encephalitis, Herpes Zoster cerebellitis, general paresis (syphilis), tuberculous meningitis, tuberculous encephalitis, optic neuritis, granulomatous angiitis, temporal arthritis, cerebral vasculitis, Spatz-Lindenberg's disease, methamphetamine-associated vasculitis, cocaine-associated vasculitis, traumatic brain injury, stroke, Lance-Adams syndrome, post-anoxic encephalopathy, radiation necrosis, limbic encephalitis, Alzheimer's disease, progressive supranuclear palsy, striatonigral degeneration, corticocobasal ganglionic degeneration, primary progressive aphasia, frontotemporal dementia associated with chromosome 17, spinal muscular atrophy, HIV-associated myelopathy, HTLV-1-associated myelopathy (Tropical Spastic Paraparesis), tabes dorsalis (syphilis), transverse myelitis, post-polio syndrome, spinal cord injury, radiation myelopathy, Charcot-Marie-Tooth, HIV-associated polyneuropathies, campylobacter-associated motor axonopathies, Guillian Barre Syndrome, chronic inflammatory demyelinating polyneuropathy, diabetic amyotrophy avulsion, phantom limb, complex regional pain syndrome, diabetic neuropathies, paraneoplastic neuropathies, myotonic dystrophy, HTLV-1-associated myopathy, trichinosis, inflammatory myopathies (polymyositis, inclusion body myositis, dermatomyositis), sickle cell disease, alpha-1-antitrypsin deficiency, tuberculosis, subacute bacterial endocarditis, chronic viral hepatitis, viral cardiomyopathy, Chaga's disease, malaria, Coxsackie B infection, macular degeneration, retinitis pigmentosa, vasculitis, inflammatory bowel disease, Crohn's disease, rheumatoid arthritis, bullous pemphigus, Churg-Strauss syndrome, myocardial infarction, toxic epidermal necrolysis, shock, type-1 diabetes, autoimmune thyroiditis, lymphoma, ovarian cancer, Lupus (systemic lupus erythematosus), asthma, progeria, sarcoidosis, type-2 diabetes and metabolic syndrome.

Other disorders that may be amenable to treatment using the mutant IL-10 of the present invention include, but are not limited to, inflammatory bowel diseases such as ileitis, ulcerative colitis and Crohn's disease; inflammatory lung disorders such as bronchitis, oxidant-induced lung injury and chronic obstructive airway disease; inflammatory disorders of the eye including corneal dystrophy, ocular hypertension, trachoma, onchocerciasis, retinitis, uveitis, sympathetic ophthalmitis and endophthalmitis; chronic inflammatory disorders of the gum including periodontitis; chronic inflammatory disorders of the joints including arthritis, septic arthritis and osteoarthritis, tuberculosis arthritis, leprosy arthritis, sarcoid arthritis; disorders of the skin including sclerodermatitis, sunburn, psoriasis and eczema; encephalomyelitis and viral or autoimmune encephalitis; autoimmune diseases including immune-complex vasculitis, and disease of the heart including ischemic heart disease, heart failure and cardiomyopathy. Other non-limiting examples of diseases that may benefit from the use of the mutant IL-10 of the invention include adrenal insufficiency; hypercholesterolemia; atherosclerosis; bone disease associated with increased bone resorption, e.g., osteoporosis, pre-eclampsia, eclampsia, uremic complications; chronic liver failure, and other disorders associated with inflammation such as cystic fibrosis, tuberculosis, cachexia, ischeimia/reperfusion, hemodialysis related conditions, glomerulonephritis, restenosis, inflammatory sequelae of viral infections, hypoxia, hyperbaric oxygen convulsions and toxicity, dementia, Sydenham's chorea, Huntington's disease, epilepsy, Korsakoff's disease, imbecility related to cerebral vessel disorder, NO mediated cerebral trauma and related sequelae, ischemic brain edema (stroke), migraine, emesis, immune complex disease, allograft rejection, infections caused by invasive microorganisms; aging, and various forms of cancer.

D. Delivery

Gene Delivery Techniques

Anti-inflammatory genes as described above, are delivered to the subject in question using any of several gene-delivery techniques. Several methods for gene delivery are known in the art. As described further below, genes can be delivered either directly to the mammalian subject or, alternatively, delivered ex vivo, to cells derived from the subject and then reimplanted in the subject.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems have been described. See, e.g., U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109. Replication-defective murine retroviral vectors are widely utilized gene transfer vectors. Murine leukemia retroviruses include a single strand RNA complexed with a nuclear core protein and polymerase (pol) enzymes encased by a protein core (gag) and surrounded by a glycoprotein envelope (env) that determines host range. The genomic structure of retroviruses includes gag, pol, and env genes enclosed at the 5' and 3' long terminal repeats (LTRs). Retroviral vector systems exploit the fact that a minimal vector containing the 5' and 3' LTRs and the packaging signal are sufficient to allow vector packaging and infection and integration into target cells provided that the viral structural proteins are supplied in trans in the packaging cell line. Fundamental advantages of retroviral vectors for gene transfer include efficient infection and gene expression in most cell types, precise single copy vector integration into target cell chromosomal DNA and ease of manipulation of the retroviral genome.

A number of adenovirus vectors have also been described. Unlike retroviruses, which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J Virol.* (1994) 68:933-940; Barr et al., *Gene Therapy* (1994) 1:51-58, Berkner, K. L. *BioTechniques* (1988) 6:616-629; and Rich et al., *Human Gene Therapy* (1993) 4:461-476). Adenovirus vectors for use in the subject methods are described in more detail below.

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875.

Additional viral vectors useful for delivering the nucleic acid molecules of interest include those derived from the pox family of viruses, including vaccinia virus and avian poxvirus. By way of example, vaccinia virus recombinants expressing the genes can be constructed as follows. The DNA encoding the particular polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the protein into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866-6869 and Wagner et al. *Proc. Natl. Acad. Sci. USA* (1992) 89:6099-6103, can also be used for gene delivery.

Members of the Alphavirus genus, such as but not limited to vectors derived from the Sindbis and Semliki Forest viruses, will also find use as viral vectors for delivering the anti-inflammatory cytokine gene. For a description of Sinbus-virus derived vectors useful for the practice of the instant methods, see, Dubensky et al., *J. Virol.* (1996) 70:508-519; and International Publication Nos. WO 95/07995 and WO 96/17072.

Alternatively, the anti-inflammatory cytokines can be delivered without the use of viral vectors, such as by using plasmid-based nucleic acid delivery systems as described in U.S. Pat. Nos. 6,413,942; 6,214,804; 5,580,859; 5,589,466; 5,763,270; and 5,693,622, all incorporated herein by reference in their entireties. Plasmids will include the gene of interest operably linked to control elements that direct the expression of the protein product in vivo. Such control elements are well known in the art.

Plasmid Gene Delivery Systems

As explained above, the gene of interest can be introduced into the subject or cells of the subject using non-viral vectors, such as plasmids, and any of the several plasmid delivery techniques well-known in the art. For example, vectors can be introduced without delivery agents, as described in, e.g., U.S. Pat. Nos. 6,413,942, 6,214,804 and 5,580,859, all incorporated by reference herein in their entireties.

Alternatively, the vectors encoding the gene of interest can be packaged in liposomes prior to delivery to the subject or to cells derived therefrom, such as described in U.S. Pat. Nos. 5,580,859; 5,549,127; 5,264,618; 5,703,055, all incorporated herein by reference in their entireties. Lipid encapsulation is generally accomplished using liposomes, which are able to stably bind or entrap and retain nucleic acid. The ratio of condensed DNA to lipid preparation can vary but will generally be around 1:1 (mg DNA:micromoles lipid) or more of lipid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527. The DNA can also be delivered in cochleate lipid compositions similar to those described by Papahadjopoulos et al., *Biochem. Biophys. Acta.* (1975) 394:483-491. See, also, U.S. Pat. Nos. 4,663,161 and 4,871,488, incorporated herein by reference in their entireties.

The vectors may also be encapsulated, adsorbed to, or associated with, particulate carriers, well known in the art. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al. (1997) *J. Microencap.* 14(2) 197-210.

Moreover, plasmid DNA can be guided by a nuclear localization signal or like modification.

Additionally, biolistic delivery systems employing particulate carriers such as gold and tungsten, are useful for delivering genes of interest. The particles are coated with the gene to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744, all incorporated herein by reference in their entireties.

A wide variety of other methods can be used to deliver the vectors. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, peptoid delivery, or microinjection. See, e.g., Sambrook et al., supra, for a discussion of techniques for transforming cells of interest; and Felgner, P. L., *Advanced Drug Delivery Reviews* (1990) 5:163-187, for a review of delivery systems useful for gene transfer. Methods of delivering DNA using electroporation are described in, e.g., U.S. Pat. Nos. 6,132,419; 6,451,002, 6,418,341, 6233, 483, U.S. Patent Publication No. 2002/0146831; and International Publication No. WO/0045823, all of which are incorporated herein by reference in their entireties.

It may also be desirable to fuse the plasmid encoding the gene of interest to immunoglobulin molecules in order to provide for sustained expression. One convenient technique is to fuse the plasmid encoding the agent of interest to the Fc portion of a mouse IgG2a with a noncytolytic mutation. Such a technique has been shown to provide for sustained expression of cytokines, such as IL-10, especially when combined with electroporation. See, e.g., Jiang et al., *J. Biochem.* (2003) 133:423-427; and Adachi et al., *Gene Ther.* (2002) 9:577-583.

Adenovirus Gene Delivery Systems

In one embodiment of the present invention, a nucleotide sequence encoding the anti-inflammatory cytokine is inserted into an adenovirus-based expression vector. The adenovirus genome is a linear double-stranded DNA molecule of approximately 36,000 base pairs with the 55-kDa terminal protein covalently bound to the 5' terminus of each strand. Adenoviral ("Ad") DNA contains identical Inverted Terminal Repeats ("ITRs") of about 100 base pairs with the exact length depending on the serotype. The viral origins of replication are located within the ITRs exactly at the genome ends. DNA synthesis occurs in two stages. First, replication proceeds by strand displacement, generating a daughter duplex molecule and a parental displaced strand. The displaced strand is single-stranded and can form a "panhandle" intermediate, which allows replication initiation and generation of a daughter duplex molecule. Alternatively, replication can proceed from both ends of the genome simultaneously, obviating the requirement to form the panhandle structure.

During the productive infection cycle, the viral genes are expressed in two phases: the early phase, which is the period up to viral DNA replication, and the late phase, which coincides with the initiation of viral DNA replication. During the early phase only the early gene products, encoded by regions E1, E2, E3 and E4, are expressed, which carry out a number of functions that prepare the cell for synthesis of viral structural proteins. During the late phase, late viral gene products are expressed in addition to the early gene products and host cell DNA and protein synthesis are shut off. Consequently, the cell becomes dedicated to the production of viral DNA and of viral structural proteins.

The E1 region of adenovirus is the first region expressed after infection of the target cell. This region consists of two transcriptional units, the E1A and E1B genes. The main functions of the E1A gene products are to induce quiescent cells to enter the cell cycle and resume cellular DNA synthesis, and to transcriptionally activate the E1B gene and the other early regions (E2, E3, E4). Transfection of primary cells with the E1A gene alone can induce unlimited proliferation (immortalization), but does not result in complete transformation. However, expression of E1A in most cases results in induction of programmed cell death (apoptosis), and only occasionally immortalization. Coexpression of the E1B gene is required to prevent induction of apoptosis and for complete morphological transformation to occur. In established immortal cell lines, high level expression of E1A can cause complete transformation in the absence of E1B.

The E1B-encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed.

Adenoviral-based vectors express gene product peptides at high levels. Adenoviral vectors have high efficiencies of infectivity, even with low titers of virus. Additionally, the virus is fully infective as a cell-free virion so injection of producer cell lines is not necessary. Adenoviral vectors achieve long-term expression of heterologous genes in vivo. Adenovirus is not associated with severe human pathology, the virus can infect a wide variety of cells and has a broad host-range, the virus can be produced in large quantities with relative ease, and the virus can be rendered replication defective by deletions in the early-region 1 ("E1") of the viral genome. Thus, vectors derived from human adenoviruses, in which at least the E1 region has been deleted and replaced by a gene of interest, have been used extensively for gene therapy experiments in the pre-clinical and clinical phase.

Adenoviral vectors for use with the present invention are derived from any of the various adenoviral serotypes, including, without limitation, any of the over 40 serotype strains of adenovirus, such as serotypes 2, 5, 12, 40, and 41. The adenoviral vectors used herein are replication-deficient and contain the gene of interest under the control of a suitable promoter, such as any of the promoters discussed below with reference to adeno-associated virus. For example, U.S. Pat. No. 6,048,551, incorporated herein by reference in its entirety, describes replication-deficient adenoviral vectors that include the human gene for the anti-inflammatory cytokine IL-10, as well as vectors that include the gene for the anti-inflammatory cytokine IL-1ra, under the control of the Rous Sarcoma Virus (RSV) promoter, termed Ad.RSVIL-10 and Ad.RSVIL-1ra, respectively.

Other recombinant adenoviruses, derived from any of the adenoviral serotypes, and with different promoter systems, can be used by those skilled in the art. For example, U.S. Pat. No. 6,306,652, incorporated herein by reference in its entirety, describes adenovirus vectors with E2A sequences, containing the hr mutation and the ts125 mutation, termed ts400, to prevent cell death by E2A overexpression, as well as vectors with E2A sequences, containing only the hr mutation, under the control of an inducible promoter, and vectors with E2A sequences, containing the hr mutation and the ts125 mutation (ts400), under the control of an inducible promoter.

Moreover, "minimal" adenovirus vectors as described in U.S. Pat. No. 6,306,652 will find use with the present invention. Such vectors retain at least a portion of the viral genome that is required for encapsidation of the genome into virus particles (the encapsidation signal), as well as at least one copy of at least a functional part or a derivative of the ITR. Packaging of the minimal adenovirus vector can be achieved by co-infection with a helper virus or, alternatively, with a packaging-deficient replicating helper system as described in U.S. Pat. No. 6,306,652.

Other useful adenovirus-based vectors for delivery of anti-inflammatory cytokines include the "gutless" (helper-dependent) adenovirus in which the vast majority of the viral genome has been removed (Wu et al., *Anesthes.* (2001) 94:1119-1132). Such "gutless" adenoviral vectors essentially create no viral proteins, thus allowing virally driven gene therapy to successfully ensue for over a year after a single administration (Parks, R. J., *Clin. Genet.* (2000) 58:1-11; Tsai et al., *Curr. Opin. Mol. Ther.* (2000) 2:515-523). In addition, removal of the viral genome creates space for insertion of control sequences that provide expression regulation by systemically administered drugs (Burcin et al., *Proc. Natl. Acad. Sci. USA* (1999) 96:355-360), adding both safety and control of virally driven protein expression. These and other recombinant adenoviruses will find use with the present methods.

Adeno-Associated Virus Gene Delivery Systems

Adeno-associated virus (AAV) has been used with success to deliver genes for gene therapy. The AAV genome is a linear, single-stranded DNA molecule containing about 4681 nucleotides. The AAV genome generally comprises an internal, nonrepeating genome flanked on each end by inverted terminal repeats (ITRs). The ITRs are approximately 145 base pairs (bp) in length. The ITRs have multiple functions, including providing origins of DNA replication, and packaging signals for the viral genome. The internal nonrepeated portion of the genome includes two large open reading frames, known as the AAV replication (rep) and capsid (cap) genes. The rep and cap genes code for viral proteins that allow the virus to replicate and package into a virion. In particular, a family of at least four viral proteins is expressed from the AAV rep region, Rep 78, Rep 68, Rep 52, and Rep 40, named according to their apparent molecular weight. The AAV cap region encodes at least three proteins, VP1, VP2, and VP3.

AAV has been engineered to deliver genes of interest by deleting the internal nonrepeating portion of the AAV genome (i.e., the rep and cap genes) and inserting a heterologous gene (in this case, the gene encoding the anti-inflammatory cytokine) between the ITRs. The heterologous gene is typically functionally linked to a heterologous promoter (constitutive, cell-specific, or inducible) capable of driving gene expression in the patient's target cells under appropriate conditions. Termination signals, such as polyadenylation sites, can also be included.

AAV is a helper-dependent virus; that is, it requires coinfection with a helper virus (e.g., adenovirus, herpesvirus or vaccinia), in order to form AAV virions. In the absence of coinfection with a helper virus, AAV establishes a latent state in which the viral genome inserts into a host cell chromosome, but infectious virions are not produced. Subsequent infection by a helper virus "rescues" the integrated genome, allowing it to replicate and package its genome into an infectious AAV virion. While AAV can infect cells from different species, the helper virus must be of the same species as the host cell. Thus, for example, human AAV will replicate in canine cells coinfected with a canine adenovirus.

Recombinant AAV virions comprising the anti-inflammatory cytokine coding sequence may be produced using a variety of art-recognized techniques described more fully below. Wild-type AAV and helper viruses may be used to provide the necessary replicative functions for producing rAAV virions (see, e.g., U.S. Pat. No. 5,139,941, incorporated herein by reference in its entirety). Alternatively, a plasmid containing helper function genes, in combination with infection by one of the well-known helper viruses, can be used as the source of replicative functions (see e.g., U.S. Pat. No. 5,622,856 and U.S. Pat. No. 5,139,941, both incorporated herein by reference in their entireties). Similarly, a plasmid containing accessory function genes can be used in combination with infection by wild-type AAV to provide the necessary replicative functions. These three approaches, when used in combination with a rAAV vector, are each sufficient to produce rAAV virions. Other approaches, well known in the art, can also be employed by the skilled artisan to produce rAAV virions.

In a preferred embodiment of the present invention, a triple transfection method (described in detail in U.S. Pat. No. 6,001,650, incorporated by reference herein in its entirety) is used to produce rAAV virions because this method does not require the use of an infectious helper virus, enabling rAAV virions to be produced without any detectable helper virus present. This is accomplished by use of three vectors for rAAV virion production: an AAV helper function vector, an accessory function vector, and a rAAV expression vector. One of skill in the art will appreciate, however, that the nucleic acid sequences encoded by these vectors can be provided on two or more vectors in various combinations.

As explained herein, the AAV helper function vector encodes the "AAV helper function" sequences (i.e., rep and cap), which function in trans for productive AAV replication and encapsidation. Preferably, the AAV helper function vector supports efficient AAV vector production without generating any detectable wt AAV virions (i.e., AAV virions containing functional rep and cap genes). An example of such a vector, pHLP19, is described in U.S. Pat. No. 6,001,650, incorporated herein by reference in its entirety. The rep and cap genes of the AAV helper function vector can be derived from any of the known AAV serotypes, as explained above. For example, the AAV helper function vector may have a rep gene derived from AAV-2 and a cap gene derived from AAV-6; one of skill in the art will recognize that other rep and cap gene combinations are possible, the defining feature being the ability to support rAAV virion production.

The accessory function vector encodes nucleotide sequences for non-AAV-derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the well-known helper viruses such as adenovirus, herpesvirus (other than herpes simplex virus type-1), and vaccinia virus. In a preferred embodiment, the accessory function plasmid pLadeno5 is used (details regarding pLadeno5 are described in U.S. Pat. No. 6,004,797, incorporated herein by reference in its entirety). This plasmid provides a complete set of adenovirus accessory functions for AAV vector production, but lacks the components necessary to form replication-competent adenovirus.

In order to further an understanding of AAV, a more detailed discussion is provided below regarding recombinant AAV expression vectors and AAV helper and accessory functions Recombinant AAV Expression Vectors Recombinant AAV (rAAV) expression vectors are constructed using known techniques to at least provide as operatively linked components in the direction of transcription, control elements including a transcriptional initiation region, the anti-inflammatory polynucleotide of interest and a transcriptional termination region. The control elements are selected to be functional in a mammalian muscle cell. The resulting construct, which contains the operatively linked components, is bounded (5' and 3') with functional AAV ITR sequences.

The nucleotide sequences of AAV ITR regions are known. See, e.g., Kotin, R. M. (1994) *Human Gene Therapy* 5:793-801; Berns, K. I. "Parvoviridae and their Replication" in *Fundamental Virology,* 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-6, AAV-7 and AAV-8, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Suitable polynucleotide molecules for use in AAV vectors will be less than about 5 kilobases (kb) in size. The selected polynucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, neuron-specific enolase promoter, a GFAP promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

The AAV expression vector which harbors the polynucleotide molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992) *Current Topics in Microbiol. and Immunol.* 158:97-129; Kotin (1994) *Human Gene Therapy* 5:793-801; Shelling and Smith (1994) *Gene Therapy* 1:165-169; and Zhou et al. (1994) *J. Exp. Med.* 179:1867-1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM MgCl2, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 μg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

For the purposes of the invention, suitable host cells for producing rAAV virions from the AAV expression vectors include microorganisms, yeast cells, insect cells, and mammalian cells, that can be, or have been, used as recipients of a heterologous DNA molecule and that are capable of growth in, for example, suspension culture, a bioreactor, or the like. The term includes the progeny of the original cell that has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97-129; and Kotin, R. M. (1994) *Human Gene Therapy* 5:793-801. Suitable homologues of the AAV rep coding region include the human herpesvirus 6 (HHV-6) rep gene which is also known to mediate AAV-2 DNA replication (Thomson et al. (1994) *Virology* 204:304-311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822-3828; and McCarty et al. (1991) *J. Virol.* 65:2936-2945. A number of other vectors have been described which encode Rep and/or Cap expression products. See, e.g., U.S. Pat. No. 5,139,941.

AAV Accessory Functions

The host cell (or packaging cell) must also be rendered capable of providing nonAAV-derived functions, or "accessory functions," in order to produce rAAV virions. Accessory functions are nonAAV-derived viral and/or cellular functions upon which AAV is dependent for its replication. Thus, accessory functions include at least those nonAAV proteins and RNAs that are required in AAV replication, including those involved inactivation of AAV gene transcription, stage specific AAV mRNA splicing, AAV DNA replication, synthesis of Cap expression products and AAV capsid assembly. Viral-based accessory functions can be derived from any of the known helper viruses.

In particular, accessory functions can be introduced into and then expressed in host cells using methods known to those of skill in the art. Typically, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241-247; McPherson et al. (1985) *Virology* 147:217-222; Schlehofer et al. (1986) *Virology* 152:110-117.

Alternatively, accessory functions can be provided using an accessory function vector as defined above. See, e.g., U.S. Pat. No. 6,004,797 and International Publication No. WO 01/83797, incorporated herein by reference in its entirety.

Nucleic acid sequences providing the accessory functions can be obtained from natural sources, such as from the genome of an adenovirus particle, or constructed using recombinant or synthetic methods known in the art. As explained above, it has been demonstrated that the full-complement of adenovirus genes are not required for accessory helper functions. In particular, adenovirus mutants incapable of DNA replication and late gene synthesis have been shown to be permissive for AAV replication. Ito et al., (1970) *J. Gen. Virol.* 9:243; Ishibashi et al, (1971) *Virology* 45:317. Similarly, mutants within the E2B and E3 regions have been shown to support AAV replication, indicating that the E2B and E3 regions are probably not involved in providing accessory functions. Carter et al., (1983) *Virology* 126:505. However, adenoviruses defective in the E1 region, or having a deleted E4 region, are unable to support AAV replication. Thus, E1A and E4 regions are likely required for AAV replication, either directly or indirectly. Laughlin et al., (1982) *J. Virol.* 41:868; Janik et al., (1981) *Proc. Natl. Acad. Sci. USA* 78:1925; Carter et al., (1983) *Virology* 126:505. Other characterized Ad mutants include: E1B (Laughlin et al. (1982), supra; Janik et al. (1981), supra; Ostrove et al., (1980) *Virology* 104:502); E2A (Handa et al., (1975) *J. Gen. Virol.* 29:239; Strauss et al., (1976) *J. Virol.* 17:140; Myers et al., (1980) *J. Viroi.* 35:665; Jay et al., (1981) *Proc. Natl. Acad. Sci. USA* 78:2927; Myers et al., (1981) *J. Biol. Chem.* 256:567); E2B (Carter, *Adeno-Associated Virus Helper Functions*, in I *CRC Handbook of Parvoviruses* (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., (1988) *J. Virol.* 62:206-210, recently reported that E1B55k is required for AAV virion production, while E1B19k is not. In addition, International Publication WO 97/17458 and Matshushita et al., (1998) *Gene Therapy* 5:938-945, describe accessory function vectors encoding various Ad genes. Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

As a consequence of the infection of the host cell with a helper virus, or transfection of the host cell with an accessory function vector, accessory functions are expressed that transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions. A "recombinant AAV virion," or "rAAV virion" is defined herein as an infectious, replication-defective virus including an AAV protein shell, encapsidating a heterologous nucleotide sequence of interest which is flanked on both sides by AAV ITRs.

Following recombinant AAV replication, rAAV virions can be purified from the host cell using a variety of conventional purification methods, such as column chromatography, CsCl gradients, and the like. For example, a plurality of column purification steps can be used, such as purification over an anion exchange column, an affinity column and/or a cation exchange column. See, for example, International Publication No. WO 02/12455. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions containing the nucleotide sequence of interest can then be used for gene delivery using the techniques described below.

D. Pharmaceutical Compositions

Optionally, the mutant IL-10 compositions of the invention may further comprise one or more pharmaceutically acceptable excipients to provide a pharmaceutical composition. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the mutant IL-10 or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, N. J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the mutant IL-10 (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the mutant IL-10 compositions described herein are in unit dosage form, meaning an amount of a conjugate or composition of the invention appropriate for a single dose, in a premeasured or pre-packaged form.

E. Administration

Exemplary methods of administration are provided for the AAV vectors and virions of the gene therapy embodiments of the present invention, with particular emphasis on embodiments directed to administration to the central nervous system (CNS) for the treatment of neurological disorders. The recombinant vectors may be introduced into any neural tissue including, without limitation, peripheral nerves, the retina, dorsal root ganglia, neuromuscular junction, as well as the CNS, e.g., to target spinal cord glial cells, using either in vivo or in vitro (also termed ex vivo) transduction techniques to treat preexisting neuronal damage. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject. Additionally, neural progenitor cells can be transduced in vitro and then delivered to the CNS.

Suitable methods for the delivery and introduction of transduced cells into a subject have been described. For example, cells can be transduced in vitro by combining recombinant vectors with cells to be transduced in appropriate media, and those cells harboring the DNA of interest can be screened using conventional techniques such as Southern blots and/or PCR, or by using selectable markers. Transduced cells can then be formulated into pharmaceutical compositions, as described above, and the composition introduced into the subject by various techniques as described below, in one or more doses.

For in vivo delivery, the recombinant vectors will be formulated into pharmaceutical compositions and one or more dosages may be administered directly in the indicated manner. Therapeutically effective doses can be readily determined by one of skill in the art and will depend on the particular delivery system used. For AAV-delivered anti-inflammatory cytokines, a therapeutically effective dose will include on the order of from about $10^6$ to $10^{15}$ of the rAAV virions, more preferably $10^7$ to $10^{12}$, and even more preferably about $10^8$ to $10^{10}$ of the rAAV virions (or viral genomes, also termed "vg"), or any value within these ranges. For adenovirus-delivered anti-inflammatory cytokines, a therapeutically effective dose will include about $1\times10^6$ plaque forming units (PFU) to $1\times10^{12}$ PFU, preferably about $1\times10^7$ PFU to about $1\times10^{10}$ PFU, or any dose within these ranges which is sufficient to alleviate the symptoms of neurodegenerative disease.

Generally, from 1 μl to 1 ml of composition will be delivered, such as from 0.01 to about 0.5 ml, for example about 0.05 to about 0.3 ml, such as 0.08, 0.09, 0.1, 0.2, etc. and any number within these ranges, of composition will be delivered.

Recombinant vectors or cells transduced in vitro may be delivered directly to neural tissue such as peripheral nerves, the retina, dorsal root ganglia, neuromuscular junction, as well as the CNS, e.g., to target spinal cord glial cells by injection into, e.g., the ventricular region, as well as to the striatum (e.g., the caudate nucleus or putamen of the striatum), spinal cord and neuromuscular junction, with a needle, catheter or related device, using neurosurgical techniques known in the art, such as by stereotactic injection (see, e.g., Stein et al., *J Virol* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 11:2315-2329, 2000).

A particularly preferred method for targeting spinal cord glia is by intrathecal delivery. Such delivery presents many advantages. The targeted protein is released into the surrounding CSF and unlike viruses, released proteins can penetrate into the spinal cord parenchyma, just as they do after acute intrathecal injections. Indeed, intrathecal delivery of viral-vectors can keep expression local. Moreover, in the case of IL-10, its brief half-life also serves to keep it local following intrathecal gene therapy; that is, its rapid degradation keeps the active protein concentrated close to its site of release. An additional advantage of intrathecal gene therapy is that the intrathecal route mimics lumbar puncture administration already in routine use in humans.

Another preferred method for administering the recombinant vectors or transduced cells is by delivery to dorsal root ganglia (DRG) neurons, e.g., by injection into the epidural space with subsequent diffusion to DRG. For example, the recombinant vectors or transduced cells can be delivered via intrathecal cannulation under conditions where the protein is diffused to DRG. See, e.g., Chiang et al., *Acta Anaesthesiol. Sin.* (2000) 38:31-36; Jain, K. K., *Expert Opin. Investig. Drugs* (2000) 9:2403-2410.

Yet another mode of administration to the CNS uses a convection-enhanced delivery (CED) system. In this way, recombinant vectors can be delivered to many cells over large areas of the CNS. Moreover, the delivered vectors efficiently express transgenes in CNS cells (e.g., glial cells). Any convection-enhanced delivery device may be appropriate for delivery of recombinant vectors. In a preferred embodiment, the device is an osmotic pump or an infusion pump. Both osmotic and infusion pumps are commercially available from a variety of suppliers, for example Alzet Corporation, Hamilton Corporation, Alza, Inc., Palo Alto, Calif.). Typically, a recombinant vector is delivered via CED devices as follows. A catheter, cannula or other injection device is inserted into CNS tissue in the chosen subject. Stereotactic maps and positioning devices are available, for example from ASI Instruments, Warren, Mich. Positioning may also be conducted by using anatomical maps obtained by CT and/or MRI imaging to help guide the injection device to the chosen target. Moreover, because the methods described herein can be practiced such that relatively large areas of the subject take up the recombinant vectors, fewer infusion cannula are needed. Since surgical complications are related to the number of penetrations, this mode of delivery serves to reduce the side-effects seen with conventional delivery techniques. For a detailed description regarding CED delivery, see U.S. Pat. No. 6,309,634, incorporated herein by reference in its entirety.

In the case of AAV-hIL-10 (F129S) therapy, for example, administration is targeted to regions of neurodegeneration where the production of anti-inflammatory cytokines would be expected to have a therapeutic effect through modulation of activated glial cells, e.g. the substantia nigra or the striatum in Parkinson's disease subjects. Similarly, therapy for MS and ALS may be intrathecally targeted.

Protein Delivery Techniques

As explained above, IL-10 mutants of the present invention can be administered alone, without gene delivery, or in conjunction with gene therapy. In addition, IL-10 mutants of the present invention can be formulated into compositions and delivered to subjects prior to, concurrent with or subsequent to delivery of one or more therapeutic agents, such as anti-inflammatory agents.

Compositions will comprise a therapeutically effective amount of the agent such that the symptoms of neurodegenerative disease are reduced, reversed, or stabilized (i.e. disease progression is slowed). The compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991). The pharmaceutical compositions may comprise the compound or its pharmaceutically acceptable salt or hydrate as the active component.

The agents may be formulated into compositions for CNS or peripheral nervous system delivery, of for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is into neural tissue including, without limitation, into peripheral nerves, the retina, dorsal root ganglia, neuromuscular junction, as well as the CNS, e.g., to target spinal cord glial or striatum cells, using any of the techniques described above with reference to recombinant vectors.

In other embodiments delivery is accomplished by methods that incorporate systemic delivery and/or materials that facilitate crossing the blood-brain barrier. Preferably, the compositions are formulated in order to improve stability and extend the half-life of the active agent. For example, the active agent, such as IL-10, can be derivatized with polyethlene glycol (PEG). Pegylation techniques are well known in the art and include, for example, site-specific pegylation (see, e.g., Yamamoto et al., *Nat. Biotech.* (2003) 21:546-552; Manjula et al., *Bioconjug. Chem.* (2003) 14:464-472; Goodson and Katre, *Biotechnology* (1990) 8:343-346; U.S. Pat. No. 6,310,180 incorporated herein by reference in its entirety), pegylation using size exclusion reaction chromatography (see, e.g., Fee, C. J., *Biotechnol. Bioeng.* (2003) 82:200-206), and pegylation using solid phase (see, e.g., Lu and Felix, *Pept. Res.* (1993) 6:140-146). For other methods of pegylation see, e.g., U.S. Pat. Nos. 5,206,344 and 6,423,685, incorporated herein by reference in their entireties, as well as reviews by Harris and Chess, *Nat. Rev. Drug. Discov.* (2003) 2:214-221; Greenwald et al., *Adv. Drug. Deliv. Rev.* (2003) 55:217-256; and Delgado et al., *Crit. Rev. Ther. Drug Carrier Syst.* (1992) 9:249-304.

Moreover, the active agent may be fused to antibodies or peptides, to improve stability and extend half-life, using techniques well known in the art. For example, the active agent may be fused to immunoglobulin molecules in order to provide for sustained release. One convenient technique is to fuse the agent of interest to the Fc portion of a mouse IgG2a with a noncytolytic mutation. See, e.g., Jiang et al., *J. Biochem.* (2003) 133:423-427; and Adachi et al., *Gene Ther.* (2002) 9:577-583. Other methods for stabilizing the agent of interest is to make the protein larger or less accessible to proteases, such as by introducing glycosylation sites and/or removing sites involved in activation (e.g., that target the protein for degradation).

Additionally, the active agent may be delivered in sustained-release formulations. Controlled or sustained-release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, the active agent can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al. (1997) *J. Microencap.* 14(2) 197-210.

III. EXPERIMENTAL

Below are examples of specific embodiments for carrying out the present invention. The examples are offered for illustrative purposes only, and are not intended to limit the scope of the present invention in any way.

Example 1

Bioactivity of rIL-10 (F129S)

Experiments were performed to compare the bioactivity of rIL-10 (F129S) to the bioactivity of wild-type rat IL-10 (rIL-10) and wild-type human IL-10 (hIL-10) in the MC/9 cell proliferation assay. COS-7 cells were transfected with plasmids expressing either wild type rIL-10, rIL-10 (F129S) or hIL-10. IL-10 in culture supernatants was quantified by ELISA and added to MC/9 cells in the amounts shown. MC/9 cell proliferation as a result of IL-10 stimulation ("bioactivity") was measured in an MTT assay. Thompson-Snipes et al. (1991) *J. Exp. Med.* 173:507-10. FIG. 2 presents the results, demonstrating the lack of bioactivity of the rIL-10-F129S in an MC/9 cell proliferation assay.

Example 2

In Vitro TNFα Secretion Activity of rIL-10 (F129S)

Experiments were performed to compare the in vitro TNFα secretion activity of rIL-10 (F129S) to the in vitro TNFα secretion activity of rIL-10 and a 1:1 mixture of rIL-10 and rIL-10 (F129S). COS-7 cells were transfected in vitro with plasmids expressing either rIL-10 or rIL-10 (F129S), or a 1:1 mixture of the two plasmids. Culture supernatants containing expressed IL-10 were added to HAPI cells stimulated with lipopolysaccharide (LPS) to induce TNFα secretion. As shown in FIG. 3, mutant and wild type rat IL-10 suppress TNFα secretion in a similar, dose-dependent manner.

Example 3

Reversal of Mechanical Allodynia by rIL-10 (F129S) In Vivo

Experiments were performed to determine whether rIL-10 (F129S) is capable of reversing mechanical allodynia in the commonly used in vivo model of chronic constriction injury (CCI) of the rat sciatic nerve. Milligan et al. (2001) *J Neurosci.* 21:2808-19. The CCI model consists of the loose ligation of the sciatic nerve at mid-thigh level with chromic gut sutures. An inflammatory reaction results, which is associated with spontaneous pain-related behavior, allodynia and hyperalgesia. Mechanical allodynia is tested by application of von Frey hairs producing a specified pressure (stimulus intensity) on the hind pad. CCI was performed on Day 1, as well as a sham surgery without nerve ligation. Allodynia developed by Day 3 as seen by increased pain sensitivity (lower stimulus intensity). Plasmids carrying rIL-10 (F129S), or green fluorescent protein (GFP) as a negative control, were injected intrathecally on Days 10 and 13. As shown in FIG. 4, allodynia was completely and persistently reversed within a few days after plasmid administration (gene therapy) with rIL-10 (F129S), but not with GFP plasmid. FIG. 4 also shows that the sham ligated rats showed no allodynia, and neither of the plasmids altered the pain response in these rats.

While certain embodiments of the invention have been illustrated and described, it will be appreciated that various changes can be made therein without departing from the spirit and scope of the invention.

The invention claimed is:

1. An isolated mutant IL-10 polypeptide, wherein the polypeptide comprises the amino acid sequence of SEQ ID NO:2 or SEQ ID NO:3 with a substitution of serine for phenylalanine at position 129 of SEQ ID NO:2 or SEQ ID NO:3.

2. A method of treating neuropathic pain in a subject comprising administering to said subject a therapeutic amount of an IL-10 polypeptide according to claim 1.

3. An isolated mutant IL-10 polypeptide, wherein the polypeptide comprises the amino acid sequence of SEQ ID NO:1.

4. The IL-10 polypeptide of claim 3, wherein the polypeptide consists of the amino acid sequence of SEQ ID NO:1.

* * * * *